United States Patent [19]

Lwoff et al.

[11] 4,369,777
[45] Jan. 25, 1983

[54] APPARATUS FOR TREATMENT OF THE COMMON COLD AND ALLERGIC RHINITIS

[75] Inventors: Andre Lwoff, Paris, France; Aaron Yerushalmi, Rehovot, Israel; Irun R. Cohen, Rehovot, Israel; Gideon B. Moshe, Rishon Le Zion, Israel; Jack Pennell, Sutton Coldfield, England

[73] Assignee: Yeda Research & Dev., Co., Ltd., Rehovot, Israel

[21] Appl. No.: 261,981

[22] Filed: May 8, 1981

[51] Int. Cl.³ ............................................ A61M 16/00
[52] U.S. Cl. .......................... 128/200.14; 128/203.27; 128/204.17; 222/146 HE; 239/373; 239/346; 261/DIG. 65; 219/273
[58] Field of Search ....................... 128/200.11, 200.14, 128/200.18, 200.21, 200.22, 203.26, 203.27, 204.13, 204.17; 222/146 HE, 146 H, 529; 239/373, 346; 261/DIG. 65, 78 A; 219/273, 214

[56] References Cited

U.S. PATENT DOCUMENTS 3,190,502  6/1965  Knibb ................................. 222/529
3,434,471  3/1969  Liston ............................. 128/203.27
4,023,718  5/1977  Forbriger et al. ................. 222/529

FOREIGN PATENT DOCUMENTS 2941132  4/1981  Fed. Rep. of Germany ....................... 128/200.21

*Primary Examiner*—Henry J. Recla
*Attorney, Agent, or Firm*—Browdy & Neimark

[57] ABSTRACT

Apparatus for delivering a stream of heated humidified air to the nasal mucosa for treatment of the common cold or allergic rhinitis comprising a container adapted to contain water, apparatus for producing a supply of air under pressure, pressurizing apparatus for applying at least a part of the supply of air under pressure to the container for causing a pressurized flow of water to issue therefrom, a remote outlet member receiving at least a portion of the supply of air under pressure and the pressurized flow of water from the pressurizing apparatus and the producing apparatus via a flexible conduit, the outlet member comprising apparatus for heating at least a portion of the supply of air and apparatus for supplying the pressurized flow of water to the supply of air after heating thereof for providing a humidified heated stream of air.

13 Claims, 8 Drawing Figures

APPARATUS FOR TREATMENT OF THE COMMON COLD AND ALLERGIC RHINITIS

The present invention relates to apparatus for medical treatment generally and more particularly to apparatus for treatment of ailments associated with the nasal mucosa, such as the common cold, (viral rhinitis) and allergic rhinitis.

The present invention seeks to provide apparatus for producing a stream of heated and humidified air to the nasal mucosa for the treatment of viral rhinitis and allergic rhinitis.

Therefore, in accordance with an embodiment of the present invention, there is provided apparatus for delivering a stream of heated and humidified air comprising a container adapted to contain water, apparatus for producing a supply of air under pressure; apparatus for heating at least a part of the supply of air and providing a stream of heated air; apparatus for applying at least a part of the supply of air under pressure to the container for causing a pressurized flow of water to issue therefrom and apparatus for combining the pressurized flows of water and heated air.

Further in accordance with an embodiment of the present invention, the heating and combining apparatus are located in an outlet member which is remotely connected to the remainder of the apparatus via an air conduit and water conduit.

In accordance with a preferred embodiment of the invention the stream of heated and humidified air is supplied to the nasal mucosa at 43° Centigrade ±0.5° Centigrade.

Additionally in accordance with an embodiment of the present invention, the combining apparatus is operative for providing a stream containing uniformly sized droplets in the size range of 4–8 micron diameter.

Still further in accordance with an embodiment of the present invention there is provided apparatus for heating the nasal mucosa of a person comprising a headset including a supporting portion mounted on the patient's head and a delivery nozzle assembly carried on the supporting portion and adapted to be maintained in a precisely predetermined position adjacent the nostrils of a person, the apparatus comprising a device for causing a stream of heated humidified air to issue from the delivery nozzle.

The invention will be more fully understood and appreciated from the following detailed description taken in conjunction with the drawings in which.

Figure 1:
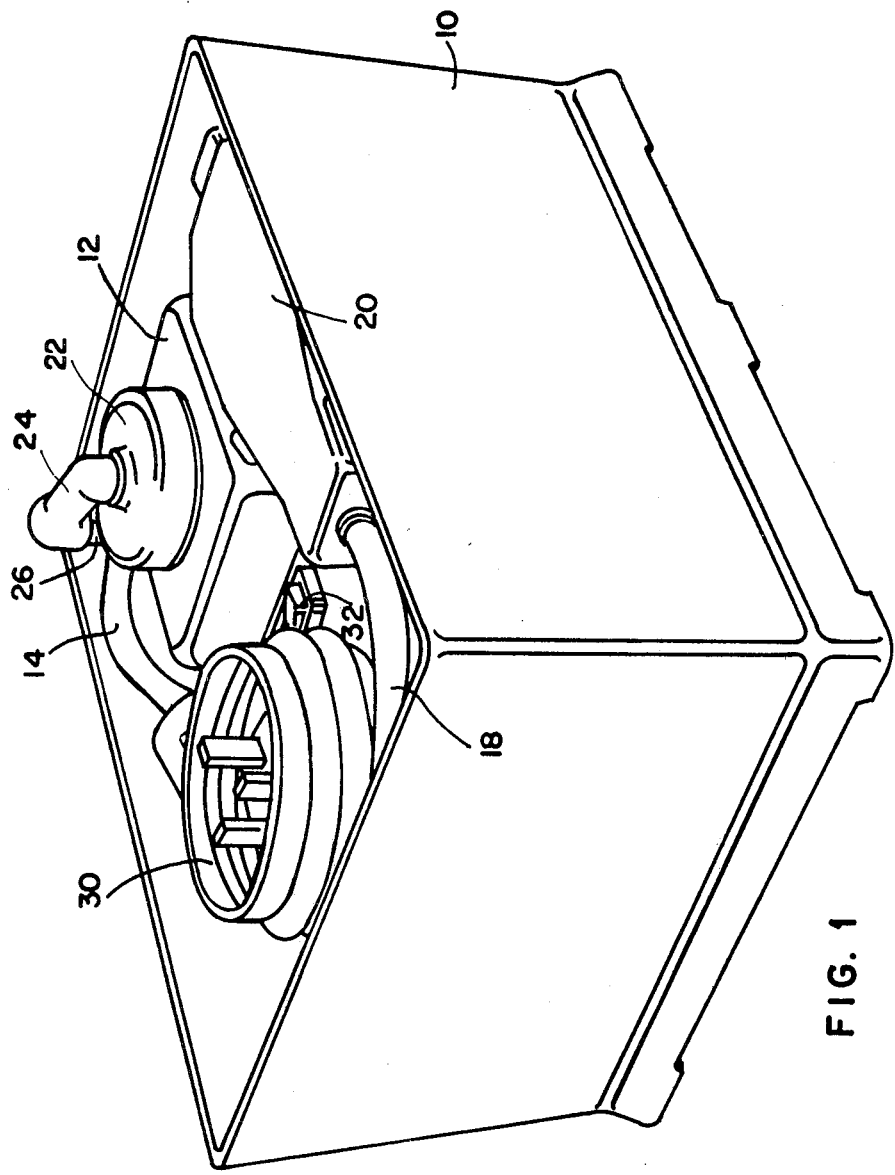
FIG. 1 is a pictorial illustration of apparatus for treatment of ailments associated with the nasal mucosa constructed and operative in accordance with the embodiment of the present invention.
Figure 2:
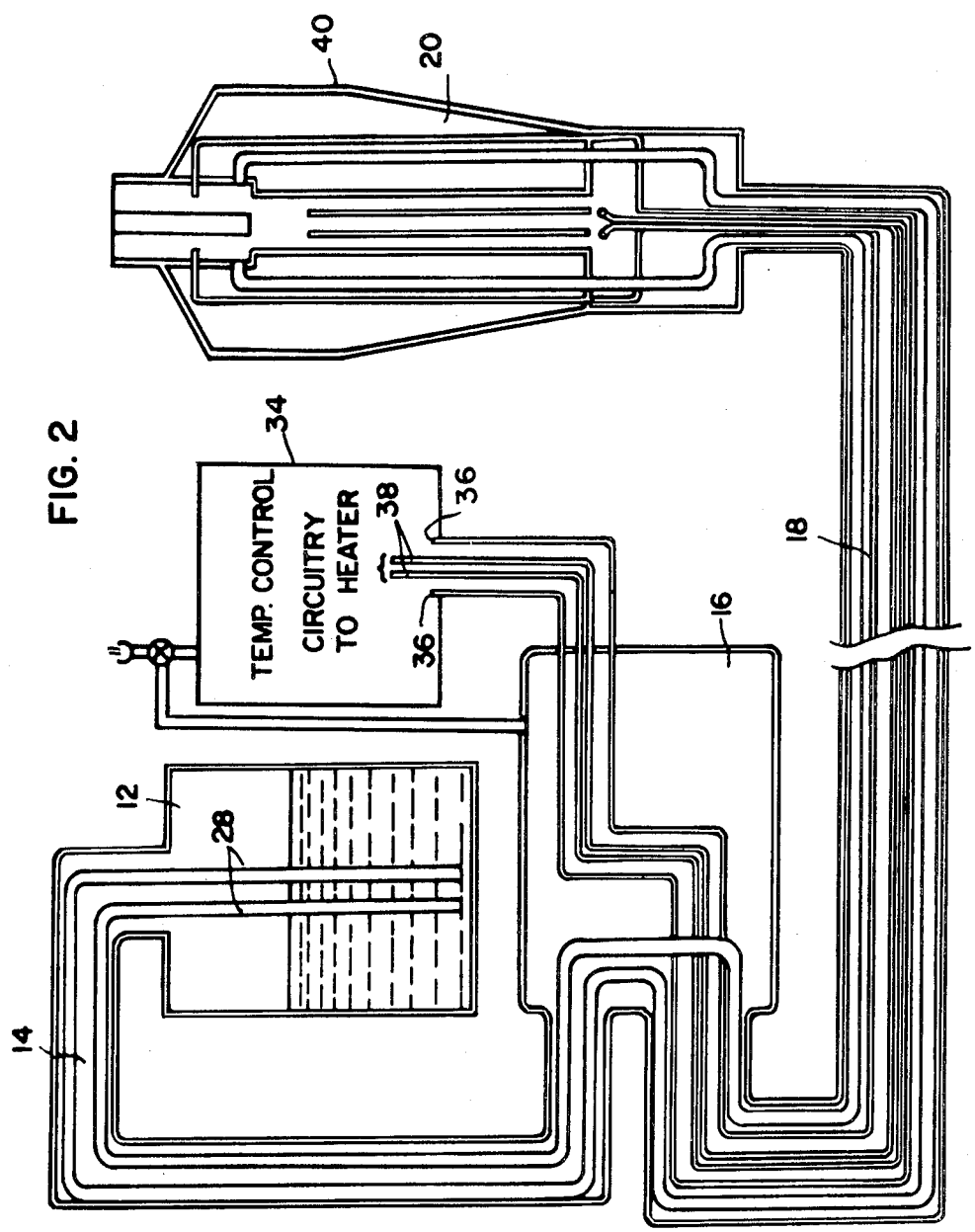
FIG. 2 is a schematic illustration of the interconnections between various component parts of the apparatus of FIG. 1.

Reference is now made to FIGS. 1 and 2 which illustrate apparatus for local heating of the nasal mucosa in the treatment of the common cold (viral rhinitis) and allergic rhinitis which is constructed and operative in accordance with an embodiment of the present invention. Disposed within a housing 10 there is provided a reservoir 12 for water or any other suitable liquid, which is coupled via a pressure sealed conduit 14 to a source of positive air pressure 16 and is also coupled via a pressure sealed conduit 18 to an outlet member 20.

Housing 10 is of generally square configuration and may be formed of a plastics material and is designed to be portable. Water reservoir 12 typically comprises a container having a removable top element 22 which forms a pressure seal with the container when in place. Pressure sealed conduit 14 may typically comprise a rigid angled portion 24 coupled to the top element 22 and a flexible portion 26 for providing pressure sealed engagement with the top element notwithstanding the required movement thereof during refilling of the reservoir 12.

Disposed within conduit 14 and extending therefrom into reservoir 12 are a pair of water supply conduits 28 which terminate adjacent the bottom of reservoir 12 and carry water under pressure of approximately 2 $Kg/cm^2$ to the outlet member 20.

It is a particular feature of the invention that the system of conduits 14 and 18 and the interiors of the water reservoir 12 and the outlet member 20 are maintained during operation under positive pressure maintained by the positive air pressure source 16 which will be described hereinafter in greater detail. Thus conduits 14 and 18 serve multiple functions, both as pressure conduits and as outer sheaths for water and electrical supply conduits which pass therethrough.

A standard electrical plug 30 arranged for engagement with a wall socket is coupled to electrical conductors and to a switch 32 which governs the operation of the apparatus. The electrical supply via switch 32 is provided to the air pressure source 16 for operation thereof and to temperature control circuitry 34 which governs the operation of heating apparatus in the outlet member 20. Temperature control circuitry 34 communicates with the outlet member via a pair of leads 36 which are coupled to temperature sensing devices located in the outlet member and via a pair of leads 38 which supply current to heating elements located in the outlet member.

Figure 3:
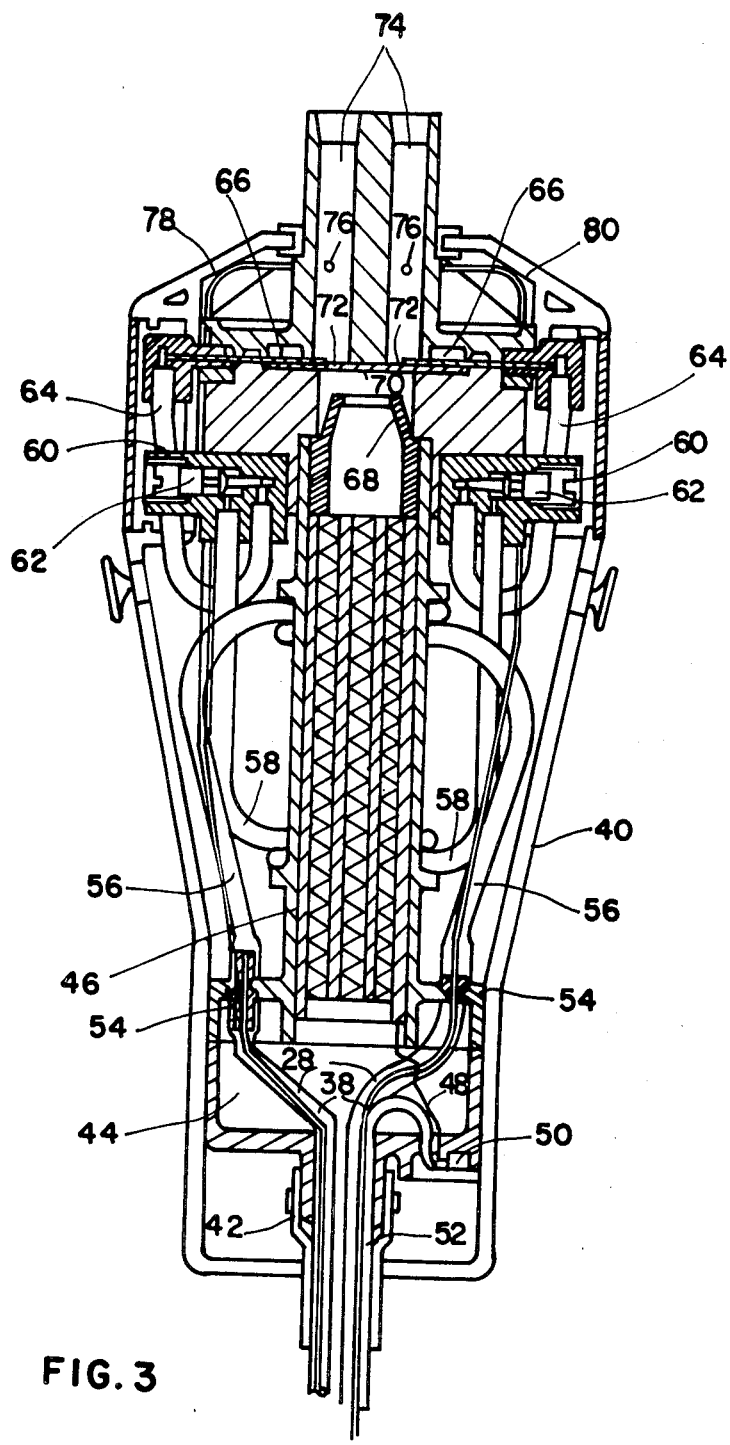
FIG. 3 is a sectional illustration of a head-mountable delivery assembly forming part of the apparatus of FIG. 1.
Figure 4:
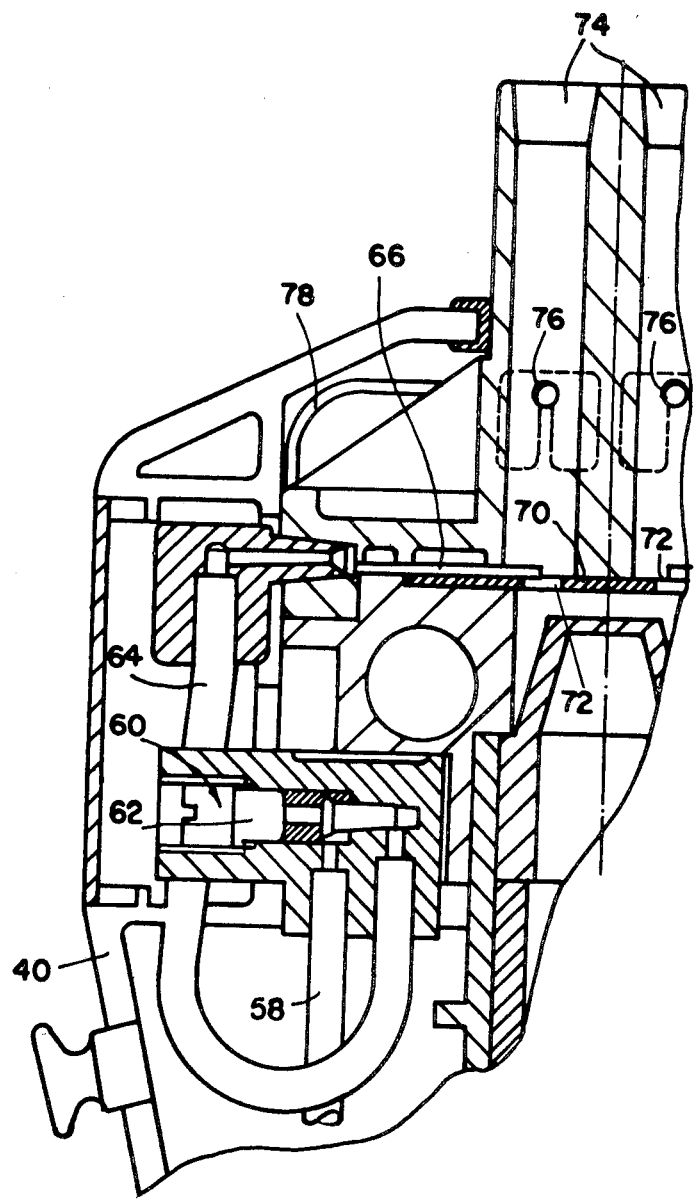
FIG. 4 is a detailed illustration of a portion of the apparatus of FIG. 3.

The construction of the outlet member 20 will now be described in detail with additional reference to FIGS. 3 and 4. It is a particular feature of the present invention that the outlet member is remotely and flexibly connected to the remainder of the apparatus and is formed with integrated heating and spray producing apparatus adjacent the delivery point of the output stream of heated humidified air.

The outlet member 20 comprises a housing 40 which may be moulded conveniently from a plastics material. Disposed within housing 40 is a connector socket 42 for securing the adjacent end of pressure sealed conduit 18 in a sealing arrangement such that an interior portion 44 of the housing 40 is in communication with the interior of conduit 18 and is maintained at a positive air pressure as desired.

A heater 46 is disposed in air flow communicating relationship with interior portion 44 so as to permit a pressurized flow of air from interior portion 44 to flow therethrough and be heated. Heater 46 receives an electrical input via a conductor 48, which is coupled at a connector 50 to an electrical current carrying wire 52 which extends thereto from conduit 18. Heater 46 is also operative to provide heating of water supplied thereto under pressure via water supply conduits 28. Water supply conduits 28 extend through interior portion 44 to respective connectors 54 which couple them to heater input conduits 56. The heated water leaves the heater via output conduits 58 which extend to respective valve asemblies 60. Valve assemblies 60 comprise screw operated stems 62 which govern the output water pressure and output water quantity. It is noted that heater 46 is formed of a heating element having longitudinally extending channels for permitting air flow therethrough.

The heated water leaves the valve assemblies 60 at a desired output pressure and is supplied via respective valve outlet conduits 64 to injection needles 66 which are disposed in opposite facing parallel orientation so as to provide a spray of heated water perpendicular to a flow of air passing therepast from heater. The flow of air passes an intermediate funnel type member 68 and a baffle 70 having a pair of air flow apertures 72 before reaching needles 66. The thus humidifed air flow then passes through twin channels 74 along which are disposed temperature measuring devices 76, such as thermocouples. The temperature measuring devices 76 are connected via conductors 78 and 80 to leads 38 for connection to the temperature control circuitry 34.

Figure 5:
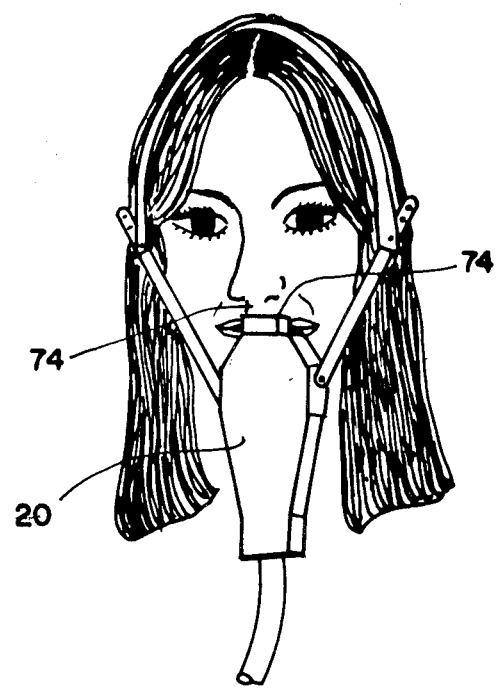
FIG. 5 is a pictorial illustration of the apparatus of FIG. 3 mounted onto the head of a patient.
Figure 6A:
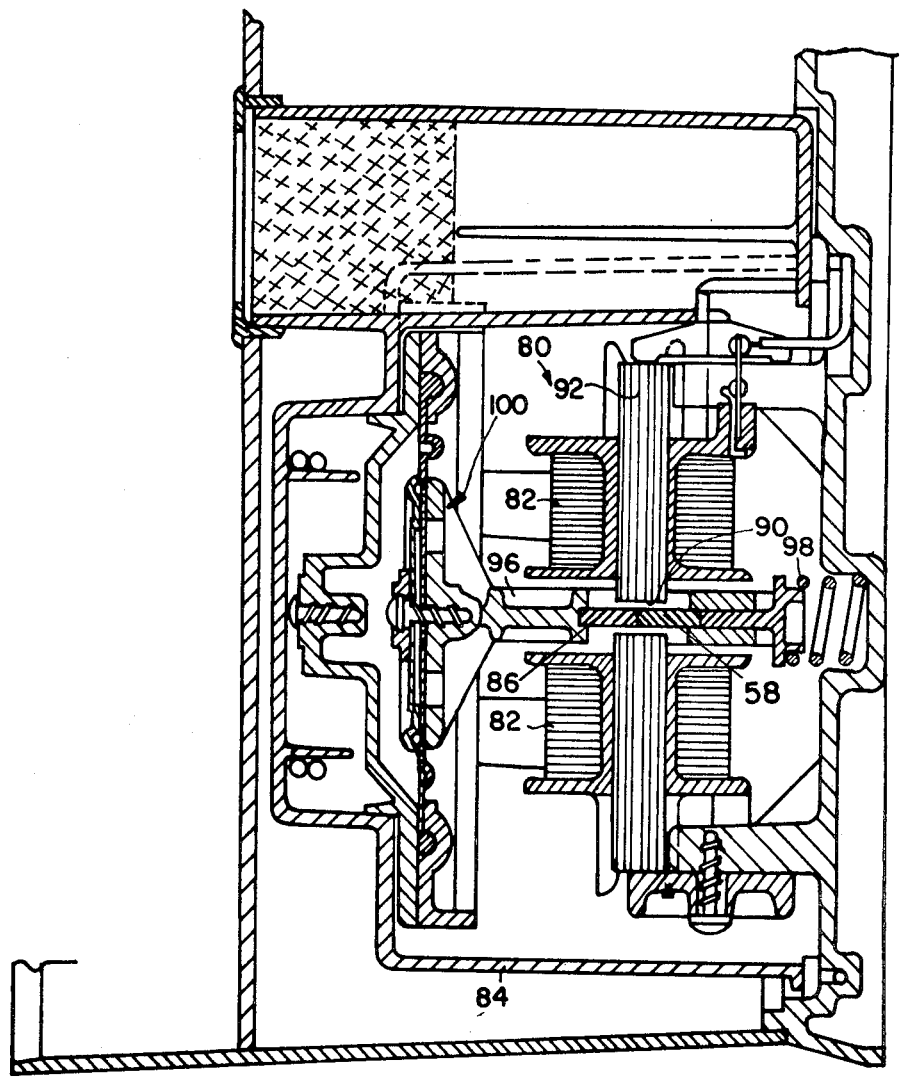
FIGS. 6A, 6B and 6C are sectional illustrations illustrating an air compressor particularly useful in the invention, the reference letters on the section lines indicating the relationship between the drawings.
Figure 6B:
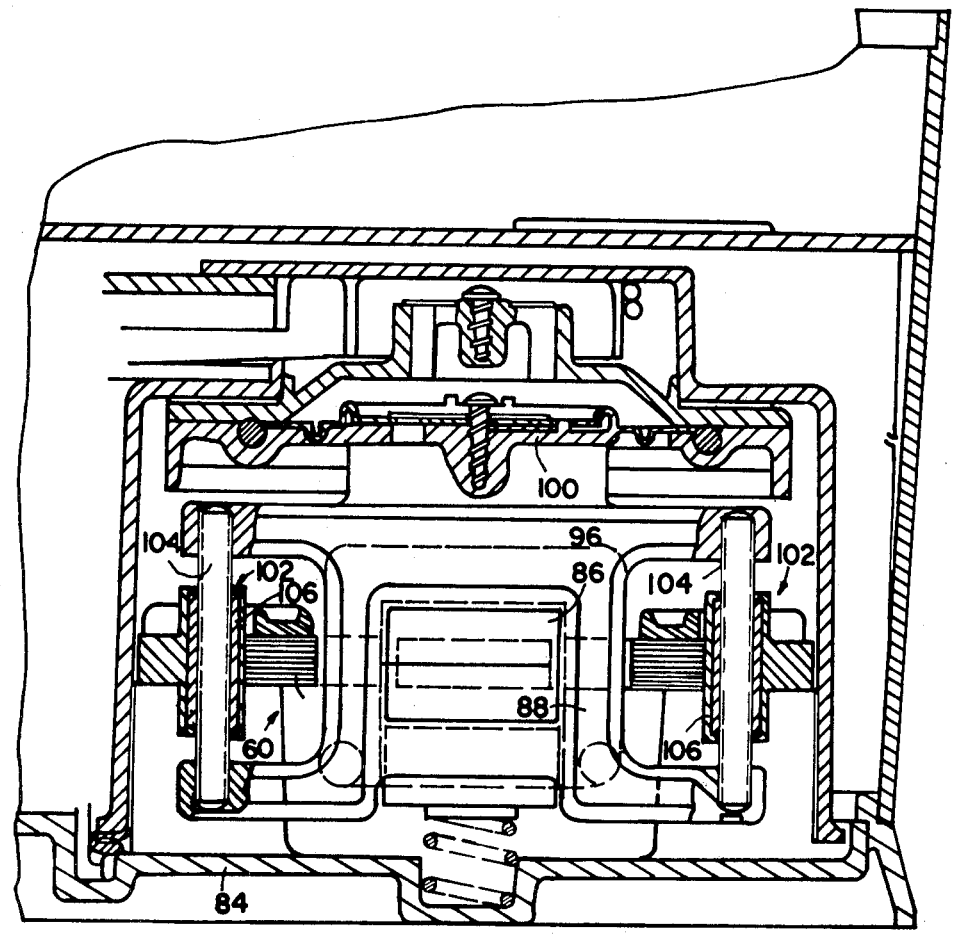
Figure 6C:
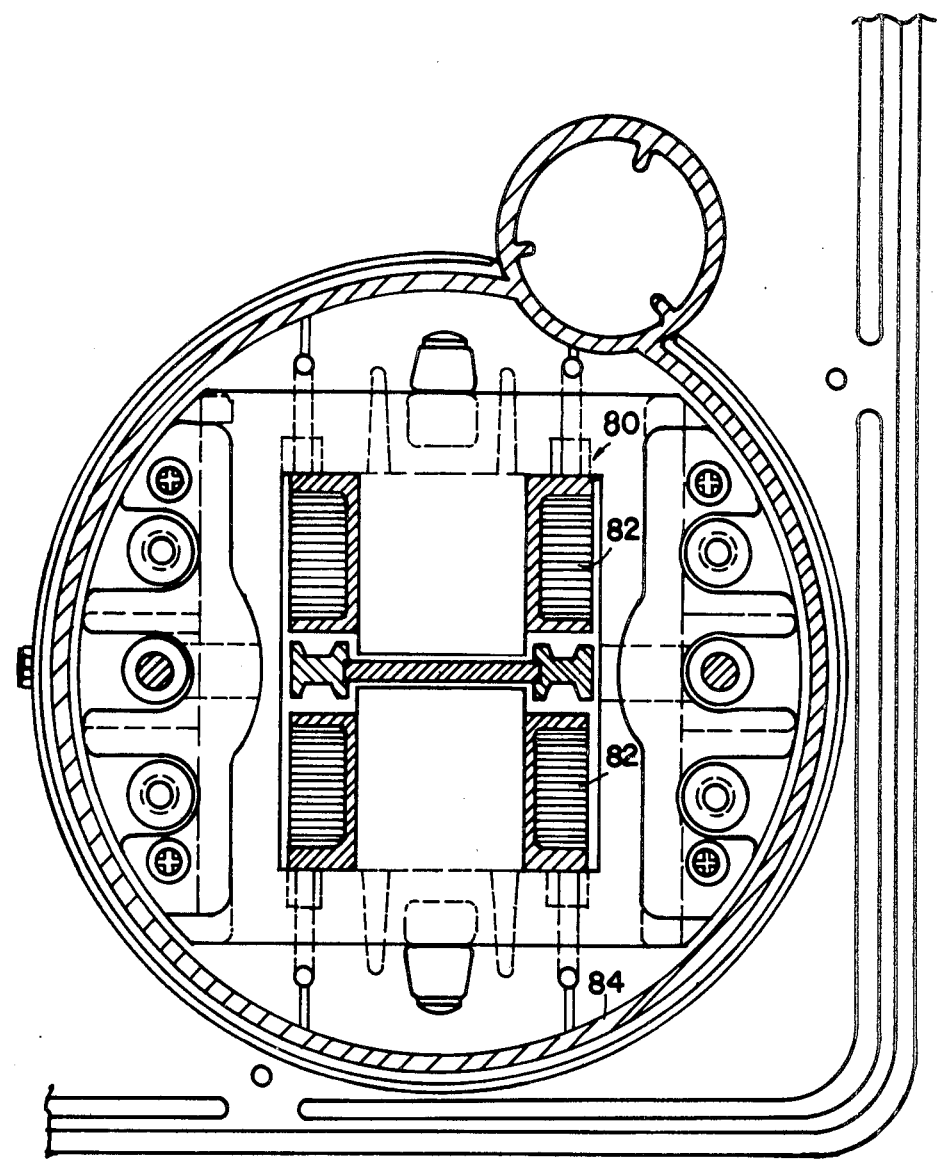

Reference is now made to FIG. 5 which illustrates the outlet member 20 of the present invention mounted on a flexible or rigid head support apparatus in a rigid manner such that the outlets of channels 74 are disposed approximately 1–1.5 cm from the nostril. A chin support (not shown) may be mounted on outlet member 20.

It is a particular feature of the present invention that in contrast to prior art devices, the outlet member is operative to direct the heated and humidified stream of air to the nasal mucosa in a manner such that the outlet member does not touch the nostrils of the patient. Furthermore it is a particular feature of the present invention and a corollary of the foregoing that the heated humidified air is not provided to the patient under pressure. Instead the kinetic energy of the stream of heated humidified air is caused to be such that it flows into the nostrils to about 3 cm without requiring inhalation by the patient. Thus it may be appreciated that the present invention does not involve inhalation, or active participation by the patient undergoing treatment.

It is also a particular feature of the present invention that generally uniform size droplets in a size range of 4–8 micron diameter are provided by the apparatus at a temperature of 43° C. plus or minus 0.5° C. in accordance with a preferred embodiment of the present invention.

It is also a particular feature of the invention, that typically an air flow of approximately 33 liters per minute is supplied to a patient's nostrils by the apparatus.

Reference is now made to FIGS. 6A, 6B and 6C which illustrate an air compressor constructed and operative in accordance with an embodiment of the present invention and useful as the source of pressurized air therefor. The compressor is characterized by relatively low power consumption while providing a stable output of pressurized air.

The compressor comprises a moving magnet motor 80 including a fixed coil 82 which is securely mounted on a housing 84. A pair of flat magnets 86 and 88 having their axes of magnetization aligned along their smallest dimension and in respective opposite directions is disposed in a gap 90 defined by the core 92 of an electromagnet 94 which includes coil 82. Magnets 86 and 88 are mounted on an armature 96 is mounted for reciprocal axial motion in gap 90. Armature 96 is mounted at one end on a spring 98 which is seated in a suitable recess formed in the housing 84, and is connected at the opposite end to a moving diaphragm pump 100 which may be of conventional construction and which will not be described in detail herein.

The motion of the armature 96 is constrained to axial motion by means of guide assemblies 102 comprising guide posts 104 which are fixedly mounted to armature 96 and which slide with respect to corresponding slidable bearing surfaces 106 which are fixed with respect to the housing.

It will be appreciated by persons skilled in the art that the invention is not limited to what has been particularly shown and described hereinabove. Rather, the scope of the invention is defined only by the claims which follow:

We claim:

1. Apparatus for delivering a stream of heated humidified air to the nasal mucosa for treatment of the common cold or of allergic rhinitis, the apparatus comprising:

a container adapted to contain water;

means for producing a supply of air under pressure;

pressurizing means for applying at least a part of said supply of air under pressure to said container for causing a pressurized flow of water to issue therefrom;

a remote outlet member comprising inlet means for receiving at least a portion of said supply of air under pressure and said pressurized flow of water from said pressurizing means and said producing means;

outlet means;

a conduit connecting said inlet means, said pressurizing means and said producing means;

means for heating at least a portion of said supply of air; and means for supplying said pressurized flow of water to said supply of air after said air is heated for providing a humidified heated stream of air;

said outlet member being adapted for positioning with respect to a user such that said outlet means is in a non-contacting adjacent position with respect to the nasal mucosa of a user for directing said humidified heated stream of air toward said nasal mucosa.

2. Apparatus according to claim 1 and wherein said outlet member also comprises means for heating said pressurized flow of water before supplying it to said supply of air.

3. Apparatus according to claim 1 and wherein said outlet member is operative for providing a generally uniformly sized spray of water droplets in said stream of air, said water droplets being in a size range of 4–8 micron diameter.

4. Apparatus according to claim 1 and wherein said outlet member also comprises temperature sensing means arranged to sense the temperature of said humidified heated stream of air.

5. Apparatus according to claim 1 and also comprising temperature control means cooperating with said temperature sensing means and said heating means for maintaining the temperature of said stream of air at a temperature above 42° C. and which does not cause appreciable patient discomfort.

6. Apparatus according to claim 5 and wherein said temperature control means is operative for maintaining said stream of air at a temperature between 42° and 44° C.

7. Apparatus according to claim 6 and wherein said temperature control means is operative for maintaining said stream of air at a temperature of 43° C. plus or minus 0.5° C.

8. Apparatus according to claim 1 and wherein said apparatus also comprises a heatset including a supporting portion mounted on a patient's head and a connecting assembly for mounting said outlet member such that said stream of air leaves said outlet member approximately 1-1.5 cm from the patient's nostrils.

9. Apparatus according to claim 1 and wherein said pressurizing means and said producing means are operative such that the kinetic energy of said stream of air is such that when released approximately 1-1.5 cm from the patient's nostrils it flows into the nostrils to about 3 cm without requiring inhalation.

10. Apparatus according to claim 1 and wherein said supplying means comprise dual water injector means.

11. Apparatus according to claim 1 and wherein said supplying means comprises means for injecting water under pressure in a direction perpendicular to the direction of flow of air leaving said heating means.

12. Apparatus according to claim 1 and wherein said producing means comprises a linear motor driven compressor including a stationary coil and core defining a gap, a pair of permanent magnets of opposite magnetization direction mounted side by side on a movable armature for reciprocal motion in said gap, a flexible diaphragm pump, and means for coupling said pump to said movable armature for driving of said pump.

13. Apparatus according to claim 1 and wherein said outlet member is operative to provide approximately 33 liters/minute of humidified heated air to a patient's nostrils.

* * * * *